(12) United States Patent
Maniruzzaman et al.

(10) Patent No.: US 10,881,616 B2
(45) Date of Patent: Jan. 5, 2021

(54) PROCESS OF PREPARING ACTIVE PHARMACEUTICAL INGREDIENT SALTS

(71) Applicants: Cubic Pharmaceuticals Ltd., Kent (GB); IKS Pharma, Kent (GB)

(72) Inventors: Mohammed Maniruzzaman, Kent (GB); Saumil Kiritkumar Bhatt, Kent (GB); Anwar Ali, Kent (GB); Arun Jangra, Kent (GB)

(73) Assignees: Cubic Pharmaceuticals Ltd., Kent (GB); University of Greenwich, London (GB)

( * ) Notice: Subject to any disclaimer, the term of this patent is extended or adjusted under 35 U.S.C. 154(b) by 0 days.

(21) Appl. No.: 16/071,671

(22) PCT Filed: Jan. 16, 2017

(86) PCT No.: PCT/GB2017/050098
§ 371 (c)(1),
(2) Date: Jul. 20, 2018

(87) PCT Pub. No.: WO2017/125720
PCT Pub. Date: Jul. 27, 2017

(65) Prior Publication Data
US 2019/0022010 A1 Jan. 24, 2019

(30) Foreign Application Priority Data
Jan. 20, 2016 (GB) .................... 1601063.9

(51) Int. Cl.
*A61K 9/16* (2006.01)
*A61K 9/20* (2006.01)
(Continued)

(52) U.S. Cl.
CPC .......... *A61K 9/1688* (2013.01); *A61K 9/1694* (2013.01); *A61K 9/2095* (2013.01);
(Continued)

(58) Field of Classification Search
None
See application file for complete search history.

(56) References Cited

U.S. PATENT DOCUMENTS

| 5,445,827 A | 8/1995 | Fritsch et al. |
| 5,631,296 A | 5/1997 | Birrenbach et al. |

(Continued)

FOREIGN PATENT DOCUMENTS

| EP | 1800667 A1 | 6/2007 |
| EP | 1905427 A1 | 4/2008 |

(Continued)

OTHER PUBLICATIONS

Patrick Makary (UK Journal of Pharmaceutical and Biosciences vol. 2(4), Jan. 4, 2014).*

(Continued)

*Primary Examiner* — Bong-Sook Baek
(74) *Attorney, Agent, or Firm* — Julie K. Staple; Dinsmore & Shohl LLP

(57) ABSTRACT

The invention relates to a process of preparing a salt of an active pharmaceutical ingredient, the process comprising providing a blend of an active pharmaceutical ingredient and a salt forming substance, mixing the blend, optionally in the presence of added water, to react the active pharmaceutical ingredient with the salt forming substance to provide the salt of the active pharmaceutical ingredient; wherein when the active pharmaceutical ingredient is acidic, the salt forming substance is a base and the pKa difference between the acidic active pharmaceutical ingredient and the base is greater than 1, typically greater than 2 or preferably greater than 3; or when the active pharmaceutical ingredient is basic, the salt forming substance is an acid and the pKa (Continued)

difference between the basic active pharmaceutical ingredient and the acid is greater than 1, typically greater than 2 or preferably greater than 3.

11 Claims, 15 Drawing Sheets

(51) Int. Cl.
    *A61K 9/48*     (2006.01)
    *A61K 47/02*     (2006.01)
    *A61K 47/10*     (2017.01)
    *A61K 47/26*     (2006.01)
    *A61K 45/06*     (2006.01)

(52) U.S. Cl.
    CPC ............ *A61K 9/4883* (2013.01); *A61K 47/02* (2013.01); *A61K 47/10* (2013.01); *A61K 47/26* (2013.01); *A61K 45/06* (2013.01)

(56) References Cited

U.S. PATENT DOCUMENTS

| | | | |
|---|---|---|---|
| 2003/0175349 A1 | 9/2003 | Garg et al. | |
| 2005/0181050 A1* | 8/2005 | Hirsh ................... | A61K 9/5026 424/469 |
| 2009/0175940 A1 | 7/2009 | Gruber | |
| 2010/0074948 A1 | 3/2010 | Ramtoola et al. | |
| 2010/0137443 A1* | 6/2010 | Carter ................. | A61K 9/0014 514/570 |
| 2011/0144207 A1 | 6/2011 | Chodankar et al. | |

FOREIGN PATENT DOCUMENTS

| EP | 2623100 A1 | 8/2013 |
|---|---|---|
| WO | WO-2006100281 A2 | 9/2006 |

OTHER PUBLICATIONS

Tayebi et al. (Iranian Journal of Pharmaceutical Research (2011), 10 (3): 469-479).*
Rahman I. (European Journal of Pharmaceutics and Biopharmaceutics 85 (2013) 1300-1309).*
Rahman II (AAPS PharmSciTech, vol. 13, No. 3:793-801, Sep. 2012).*
Zimmer, L. et al., Application of ß-Cyclodextrin in the Formulation of ODT Tablets Containing Ibuprofen, Polimery w Medycynie, 44: 231-235, 2014.
Examination Report under Section 18(3), GB Application No. GB1601063.9, dated Feb. 3, 2020.

* cited by examiner

Configuration I                Configuration II

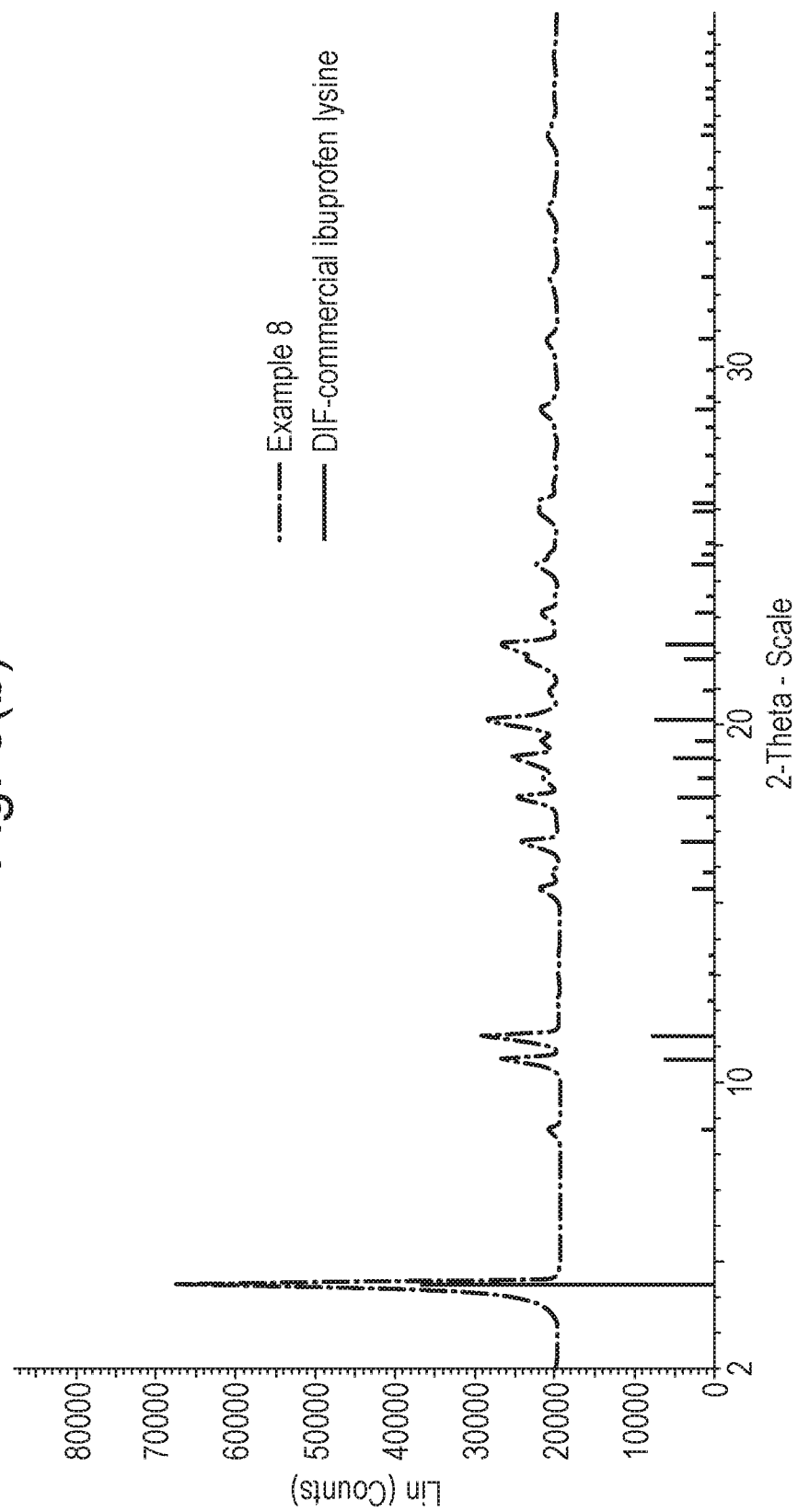

Fig. 14

| 2-Theta position | | |
|---|---|---|
| KTZ | OXA | KTZ OXA |
| 6.5 | 14.9 | 11.9 |
| 7.2 | 18.8 | 13.2 |
| 10.5 | 22.9 | 17.7 |
| 15.9 | 24.5 | 18.4 |
| 17.3 | 27.2 | 19.9 |
| 17.4 | 29.1 | 20.4 |
| 19.2 | 31.0 | 21.8 |
| 19.6 | 33.1 | 25.3 |
| 19.9 | 37.4 | 28.0 |
| 20.2 | 38.8 | 28.1 |
| 20.2 | 42.1 | 29.8 |
| 20.5 | | |
| 21.1 | | |
| 21.3 | | |
| 23.6 | | |
| 27.4 | | |

PROCESS OF PREPARING ACTIVE PHARMACEUTICAL INGREDIENT SALTS

The invention relates to processes of preparing salts of active pharmaceutical ingredients and the active pharmaceutical ingredient salts obtained/obtainable therefrom.

BACKGROUND TO THE INVENTION

Over the last decade, there has been an increased interest in crystal engineering (e.g. salts) research to enhance drug solubility and mechanical properties. About 40% of the drugs in the discovery pipeline are failing out due to poor solubility with massive inherent costs (projected about £20 billion a year) and lengthy time. Thus, there is a clear market need to develop methods to make drugs more soluble.

SUMMARY OF THE INVENTION

According to one aspect, the present invention provides a process of preparing a salt of an active pharmaceutical ingredient, the process comprising providing a blend of an active pharmaceutical ingredient and a salt forming substance, mixing the blend, optionally in the presence of added water, to react the active pharmaceutical ingredient with the salt forming substance to provide the salt of the active pharmaceutical ingredient; wherein when the active pharmaceutical ingredient is acidic, the salt forming substance is a base and the pKa difference between the acidic active pharmaceutical ingredient and the base is greater than 1, typically greater than 2 or preferably greater than 3; or when the active pharmaceutical ingredient is basic, the salt forming substance is an acid and the pKa difference between the basic active pharmaceutical ingredient and the acid is greater than 1, typically greater than 2 or preferably greater than 3.

In some embodiments, the process is carries out in the absence of any added water.

The inventors completed a multi-disciplinary study involving continuous manufacturing (CM) of pharmaceutical salts to tackle the above-mentioned needs. Batch processes are high in cost and time intensive with low plant productivity. Thus, a CM process eliminating intermediate steps improves product quality assurance. The process of the invention is employed to manufacture salts of poorly water soluble weak acidic/basic drugs in presence of a second component(s), i.e. a salt forming substance, such as a base without any addition of solvents. The process is easy to scale up, economically practical and solvent free (with an option to use liquid if required) providing a process with fewer processing steps. As well as saving time and costs, the process of the invention can dramatically reduce building, energy and carbon footprints. In addition, the present invention provides a process that entirely fits within the regulatory priority remit by providing state-of-the-art experimental techniques tuned to the current problems of pharmaceutical salts manufacturing and scale up.

The process of the invention also provides, for the first time, a feasible way of manufacturing, preferably continuously manufacturing, salts of various water insoluble drugs (e.g. ibuprofen, phenytoin, diclofenac, and indomethacin) and thereby increase the feasibility of otherwise unusable drugs.

In the process of the present invention, the active pharmaceutical ingredient and the salt forming substance are subjected to dispersive and disruptive mixing that results in the generation of sufficient torque and shear force that enable them to react to form a salt compound. This is not the same as preparing co-crystals. Co-crystallisation, rather than reaction to form a salt compound, will typically take place when the pKa difference between an active pharmaceutical ingredient and a co-crystal forming substance is less than 1.

In the pharmaceutical industry, salt formation approach is commonly used for an ionizable drug to increase solubility and dissolution rate. Salts are formed via proton transfer from an acid to a base. A stable ionic bond can be formed when the difference of pKa between an acid and a base (pKa) is greater than 1, typically greater than 2 and preferably greater than 3. The counter ion containing salt changes the pH at the dissolving surface of a salt particle in the diffusion layer, resulting in a higher dissolution rate of the salts compared with that of the corresponding free forms. According to the Henderson-Hasselbalch equations, the change of pH highly influences the aqueous solubility of an ionizable drug. In theory, the solubility of a weak basic drug increases exponentially with decreasing pH at the pH range between its pKa and pH max (pH of maximum solubility in the pH-solubility profile).

In one embodiment, when the active pharmaceutical ingredient is an acid, e.g. a weak acidic drug (e.g. ibuprofen or phenytoin), the salt forming substance may be a base having a pKa value of more than 7 or above. These bases may be selected from the group consisting of sodium hydroxide, potassium hydroxide, sodium carbonate, potassium carbonate, sodium glycinate, sodium lysinate, sodium glycinate monohydrate, N-methylglucosamine, potassium glycinate and tribasic sodium and potassium phosphates. When an amino acid such as L-Arginine is used as the salt forming agent with an acidic active pharmaceutical ingredient (e.g. ibuprofen) the pKa of the salt forming agent is typically less than 7. When a dicarboxylic acid (e.g. oxalic acid) or a benzoic sulfimide (e.g saccharin) is used as a salt forming agent with a weakly basic active pharmaceutical ingredient (e.g. ketoconazole or lamotrigine), the pKa of the salt forming agent is typically less than 7.

In one embodiment, when the active pharmaceutical ingredient is a base, e.g. a weak basic drug (e.g. propranolol, cetirizine or diphenhydramine), the salt forming substance may an acid having a pKa value lower than the active pharmaceutical ingredient (the pKa difference being more than 3).

In one embodiment, the mixing is carried out in a twin-screw extruder, a single screw extruder or a granulator.

In one embodiment the mixing is conducted with only one salt forming substance/excipient (e.g a base for acidic drug and an acid for a basic drug).

In one embodiment, the process does not comprise adding additional water or solvent.

In one embodiment, the process does not comprise a drying step.

In one embodiment, the process does not comprise a further granulation or micronization step.

In one embodiment, the mixing step provides the salt of the active pharmaceutical ingredient in powder form, preferably in free flowing powder form.

In one embodiment, the process further comprises manufacturing tablets or capsules with the salt of the active pharmaceutical ingredient with or without the addition of pharmaceutically acceptable excipients.

In one embodiment, the process further comprises manufacturing tablets or capsules with the salt of the active pharmaceutical ingredient with or without the addition of a hydrophilic polymer, super disintegrant, glidant, filler, lubricant, or combination thereof.

Suitable hydrophilic polymers include hydroxypropyl methyl cellulose, polyvinyl caprolactam, polyvinyl acetate, polyethylene glycol graft copolymer, vinylpyrrolidone-vinyl acetate copolymers, copolymer based on dimethylaminoethyl methacrylate, butyl methacrylate, and methyl methacrylate, anionic copolymer based on methacrylic acid and ethyl acrylate, N-vinyl-2-pyrrolidone and vinyl acetate copolymer.

Suitable superdisintegrants include polyplasdone crossprovidone superdisintegrants, polyplasdone crossprovidone, croscarmellose sodium, L-HPC, crospovidone CL-SF, crospovidone CL-MF, F-Melt, sodium starch glycolate, soy polysaccharide, cross-linked alginic acid, gellan gum, xanthan gum, calcium silicate, and ion exchange resins.

Suitable glidants and lubricants include magnesium stearate, $SiO_2$, talc, PRUV, glyceryl monostearate, glyceryl tribehenate, glyceryl dibehenate, sorbitan monostearate, sucrose monopalmitate, and glyceryl dibehenate.

Suitable fillers/binders include lactose, sorbitol, mannitol, starch, MCC, starlac, corn starch, carnuba wax, alginate, tribasic calcium phosphate, and dibasic calcium phosphate.

In one embodiment, a powder of the salt of the active pharmaceutical ingredient is directly compressed to provide a tablet.

In one embodiment, a powder of the salt of the active pharmaceutical ingredient is blended with a lubricant and then directly compressed to provide a tablet.

In one embodiment, the tablet is an orally disintegrating tablet.

In one embodiment, the process is a continuous process.

In one embodiment, a powder form of the salt of the active pharmaceutical ingredient is mixed with one or more pharmaceutically acceptable excipient to provide a sachet formulation.

Suitable excipients for a sachet formulation include sugar polyols (e.g. sorbitol, mannitol, xylitol, StarLac®), sucrose, lactose, PEG 2000-4000, sodium alginate, MCC, citric acid, carbomers (e.g. Ashland 940/980 and 941/981, Carbopol® SMART 1000/2000 Polymer, carbopol aquapolymer), poloxamers (e.g. Lutrol F68 (poloxamer 188), Pluronic F127, poloxamer 407, Kolliphor P407, Lutrol F108), methyl p-hydroxybenzoate, propyl p-hydroxybenzoate, aspartame, saccharin, sodium hydroxide, sodium benzoate, flavourants (e.g. strawberry, mint, vanilla, raspberry flavourants), colouring agents (e.g. iron oxide, ferric oxide, iron oxide yellow, iron oxide red, HPMC pthalate, FD&C blue (indigo carmine, brillian blue), FD&C Yellow (sunset yellow), titanium dioxide) and combinations thereof.

When carrying out the invention, a number of process features can be optimised in order to provide an improved process. Such features include the process temperature, the stoichiometric ratios of the active pharmaceutical ingredient and the salt forming substance, and the amount of torque, shear force/stress applied to the mixing step, e.g. the screw configuration or speed of an extruder.

In one embodiment, the process is carried out at a temperature of from ambient or more preferably from about 40° C. to about 200° C. To some extent, the temperature depends on the active pharmaceutical ingredient(s) and the salt forming substance being used. Suitable temperatures are provided below in the context of ibuprofen and a combination of diclofenac/phenytoin.

In some embodiments the process is carried out at a temperature of 100° C. or more, e.g. 110° C. or more, 120° C. or more, 140° C. or more, or 150° C. or more.

In one embodiment the total amount of salt forming substance or substances is 50 mol % or more, e.g. 60 mol % or more, 70 mol % or more, 80 mol % or more, 90 mol % or more, or 100 mol % or more, based on the amount of the active pharmaceutical agent.

In one embodiment, the total amount of salt forming substance or substances is 500 mol % or less, e.g. 400 mol % or less or 300 mol % or less, based on the amount of the active pharmaceutical agent.

In one embodiment, the process is carried out in a single or twin screw extruder at a screw speed of from about 50 to about 100 rpm.

In some embodiments, the process is carried out in a twin screw extruder with a heated barrel. Typically, in such embodiments, at least a portion of the heated barrel is heated to a temperature of 100° C. or more, e.g. 110° C. or more, 120° C. or more, 140° C. or more, or 150° C. or more. The twin screw extruder may be configured to facilitate dispersive and/or distributive mixing. Typically, in such embodiments, the twin screw extruder is configured to generate shear force and stress inside the heated barrel. Such configurations can be achieved by using extruder screws having a 50°-70° (e.g. 60°) forward mixing block directly adjacent to a 20°-40° (e.g. 30°) forward mixing block, and an 80°-100° (e.g. 90°) mixing block directly adjacent to the 50°-70° forward mixing block. The 20°-40° forward mixing block, 50°-70° forward mixing block and 80°-100° mixing block may be of approximately equal lengths.

Advantages of the process of the present invention, particularly in embodiments having the screw configurations and/or processing parameters (e.g. screw speed, temperatures) described herein, include greater scale of salt production, improved rate of salt production, improved particle size and/or flowability of the salt produced.

In some embodiments of the process of the present invention, a salt of an active pharmaceutical ingredient is produced at a scale of 0.5-3 kg/hr or more, typically 5 kg/hr or more, preferably 7 kg/h or more. For example, in some embodiments. the process may be carried out over 1 hour or more, (e.g. 3 hours or more, 5 hours or more, or 7 hour or more) with 0.5-3 kilos or more, typically 5 kilos or more, preferably 7 kilos or more of salt being produced per hour of processing time.

In some embodiments of the process of the present invention, the rate of production of the salt form is such that the residence time distribution (RTD) and/or mean residence time (MRT) is 90 seconds or less, typically 60 seconds or less, preferably 45 seconds or less. As used herein, residence time a measure of the time material is present in a mixer. In embodiments where the mixer is an extruder (e.g. single screw extruder or twin screw extruder), the residence time is typically the time taken for material to pass through the die from the point of feeding into the barrel. Therefore, the residence time indicates how fast the process can be conducted and, when material in the mixer is subjected to heating, what will be the likely exposure time of the drug in heated condition. The process of the present invention allows even heat-unstable drugs (e.g. omeprazole) to be processed at elevated temperatures, due to the high rate of production and low residence times.

In some embodiments, the process is carried out at elevated temperature (e.g. 100° C. or more, 110° C. or more, 120° C. or more, 140° C. or more, or 150° C. or more), in order to promote evaporation of free water (including water generated during the salt formation reaction). This enables production of a salt of a pharmaceutically active substance in substantially dry form with improved flowability, even without a subsequent drying step. Thus, the process may be for the production of a salt of a pharmaceutically active substance in a form suitable for further processing even in the absence of a subsequent drying step. In some embodiments, the salt produced by the process of the present invention has a flowability (Carr's index) of 15 or less. In some embodiments the salt produced by the process of the present invention has a Carr's index of 5-15, e.g. 8-15.

In some embodiments the salt produced by the process of the present invention has an average particle size of 250 microns or less, typically 150 microns or less, preferably 100 microns or less. In some embodiments, the salt produced by the process of the present invention has an average particle size of 100 to 150 microns. In some embodiments the salt produced by the process of the present invention has an average particle size suitable for tabletting without the need for any additional processing steps between collection of the product of the mixing step and tabletting of the product. Thus, the process may be for the direct production of a salt of a pharmaceutically active substance in a form suitable for tabletting. As used herein, the average particle size may be the mass mean diameter (MMD).

According to a further aspect, the invention provides a salt of an active pharmaceutical ingredient obtained/obtainable by a process as defined herein.

According to a further aspect, the invention provides a tablet or capsule obtained/obtainable by a process as defined herein.

According to a further aspect, the invention provides a sachet formulation obtained/obtainable by a process as defined herein.

In some embodiments, the sachet formulation of the invention is in the form of a solid dry syrup.

According to a further aspect, the present invention provides a method of treatment of the human or animal body by therapy, comprising administration to a subject of a capsule, tablet or sachet formulation as defined herein.

In some embodiments, the method of treatment comprises addition to a sachet formulation of the invention of 5-10 ml of water (e.g. reconstitution of a solid dry syrup of the invention), prior to administration.

In some embodiments, the method of treatment comprises administration of the salt of the active pharmaceutical ingredient at a dose of 5-200 mg, preferably 5-100 mg, more preferably 5-20 mg.

According to a further aspect, the present invention provides a sachet comprising a sachet formulation as defined herein.

According to a further aspect, the present invention provides a capsule, tablet or sachet formulation for use in the method of treatment described herein.

According to a further aspect, the present invention comprises use of a salt form of an active pharmaceutical ingredient in the manufacture of a medicament for use in the method of treatment defined herein.

BRIEF DESCRIPTION OF THE FIGURES

FIG. 5(b) shows XPRD diffractograms of, from top to bottom, Example 8 and commercially available ibuprofen lysine

FIG. 14 identifies 2-theta positions of peaks in XRD diffractograms of ketoconazole (KTZ), oxalic acid (OXA) and ketoconazole oxalate salt (KTZ/OXA) prepared according to the process of the present invention.

EXAMPLES

The following substances are used:

| Ingredients | Chemical Name |
| --- | --- |
| Ibuprofen | (RS)-2-(4-(2-methylpropyl)phenyl) propanoic acid |
| Diclofenac | 2-[(2,6-dichlorophenyl)amino] benzeneacetic acid |
| Phenytoin | 5,5-diphenylimidazolidine-2,4-dione |
| Tranilast | 2-{[(2E)-3-(3,4-dimethoxyphenyl)prop-2-enoyl]amino}benzoic acid |

-continued

| Ingredients | Chemical Name |
|---|---|
| Ketoconazole | 1-[4-(4-{[(2R,4S)-rel-2-(2,4-dichlorophenyl)-2-(1H-imidazol-1-ylmethyl)-1,3-dioxolan-4-yl]methoxyl}phenyl)piperazin-1-yl]ethan-1-one |
| Lamotrigine | 6-(2,3-dichlorophenyl)-1,2,4-triazine-3,5-diamine |
| Lactose | β-D-galactopyranosyl-(1→4)-D-glucose |
| Sorbitol | (2S,3R,4R,5R)-Hexane-1,2,3,4,5,6-hexol |
| Pearlitol | Mannitol |
| MCC | Microcrystalline cellulose |
| Xl 10 | Polyplasdone crossprovidone superdisintegrants |
| Xl | Polyplasdone crossprovidone superdisintegrants |
| Vivasol | Croscarmellose sodium |
| Kollidon Cl-SF | Crospovidone CL-SF |
| Kollidon Cl-MF | Crospovidone CL-MF |
| PRUV | Sodium Stearyl Fumarate |
| MgSt | Magnesium stearate |
| SiO2 | Silica dioxide |

Blending

The active pharmaceutical ingredient/salt forming substance (base or acid) powder blends in various concentrations (% w/w) were mixed thoroughly for 10 min using a turbula TF2 mixer (Basel, Switzerland) to form a homogeneous powder prior to the hot-melt extrusion (HME) processing.

Process

Figure 1:
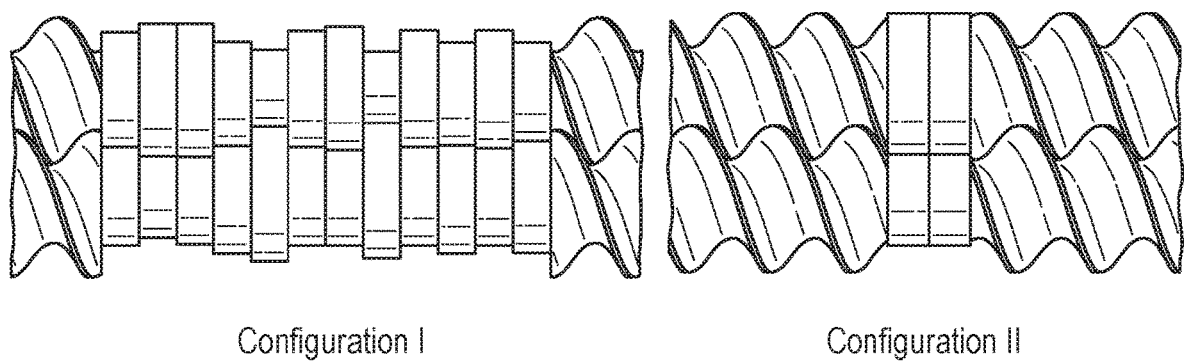
FIG. 1 illustrates screw configurations used in the process of the present invention.

Extrusion was carried out using a 16 mm co-rotating twin screw extruder (Eurolab, Thermo Scientific, UK) having length-to-diameter ratio of 40:1, with two different extruder screw configurations for ensuring distributive and dispersive mixing of the active pharmaceutical ingredient and salt forming substance in order to facilitate the interactions. The extruder was operated without a die. Feeding material was fed into the extruder at a rate of 0.5-7 kg/h using a gravimetric twin screw feeder (Brabender, Germany) at three different extruder barrel temperature profiles (120° C. for ibuprofen, 180° C. for diclofenac) at screw speeds of 50-100 rpm. Extruder screw configurations were selected to achieve a range of shearing intensities (Table 1 and FIG. 1).

TABLE 1

Screw configurations for the manufacture of salts

| Screw Configuration I | | Screw Configuration II | |
|---|---|---|---|
| Length (D) | Element/Blocks type | Length (D) | Element/Blocks type |
| 11 | Forward conveying | 19 | Forward conveying |
| 1 | 30° forward mixing | 1 | 30° forward mixing |
| 1 | 60° forward mixing | 1 | 60° forward mixing |
| 1 | 90° mixing | 1 | 90° mixing |
| 6 | Forward conveying | 2 | Forward conveying |
| 1.5 | 60° forward mixing | 0.5 | 0° mixing |
| 8 | Forward conveying | 1 | Forward conveying |
| 1 | 60° forward mixing | 0.5 | 0° mixing |
| 2 | 90° forward mixing | 2 | Forward conveying |
| 6 | Forward conveying | 0.5 | 0° mixing |
| 1.5 | Discharge | 1 | Forward conveying |
| | | 0.5 | 0° mixing |
| | | 2 | 90° |
| | | 6.5 | Forward conveying |
| | | 1.5 | Discharge |

D = 16 mm conveying block

The process a) involves the processing of the active ingredients (either acidic or basic) with a wide range of acids/bases with a pKa difference of more than 3 in the active pharmaceutical ingredient/salt forming substance (base or acid) in a binary blend with an option for tarnary mixture, b) does not require the use of water or organic solvents (e.g lower alcohols) to facilitate the exothermic reaction, c) does not require a drying process for the obtained granules of the salts, d) the shear force and mechanical energy produced inside the barrel aided by the temperature get the drug to react with base to form salts and d) it does not require further granule micronization.

Typically the granules are produced by forming solid bridges through the following mechanisms: a) partial melting (or complete) of the drug substance when drug/inorganic excipient blends are used due to the high temperature and torque applied during the process. The drug then interacts with the inorganic excipient through a proton exchange and when the temperature is relieved (late barrel zones) crystallization will take place and bind the particles together.

Inorganic excipients are mainly the base or weak acids and are referred as salt forming substances herein. For an example, for weak acidic drug (e.g. ibuprofen of phenytoin) inorganic excipients are mainly referred to those bases having pKa values more than 7 or above. These bases are selected from the group consisting of sodium hydroxide, potassium hydroxide, sodium carbonate, potassium carbonate, sodium glycinate, sodium lysinate, L-arginine, sodium glycinate monohydrate, N-methylglucosamine, potassium glycinate and tribasic sodium and potassium phosphates. For weak basic drug (e.g. propranolol, cetirizine or diphenhydramine), inorganic excipients are mainly referred to acids having lower pKa values than the drugs (the pKa difference is more than 3).

Figure 2:
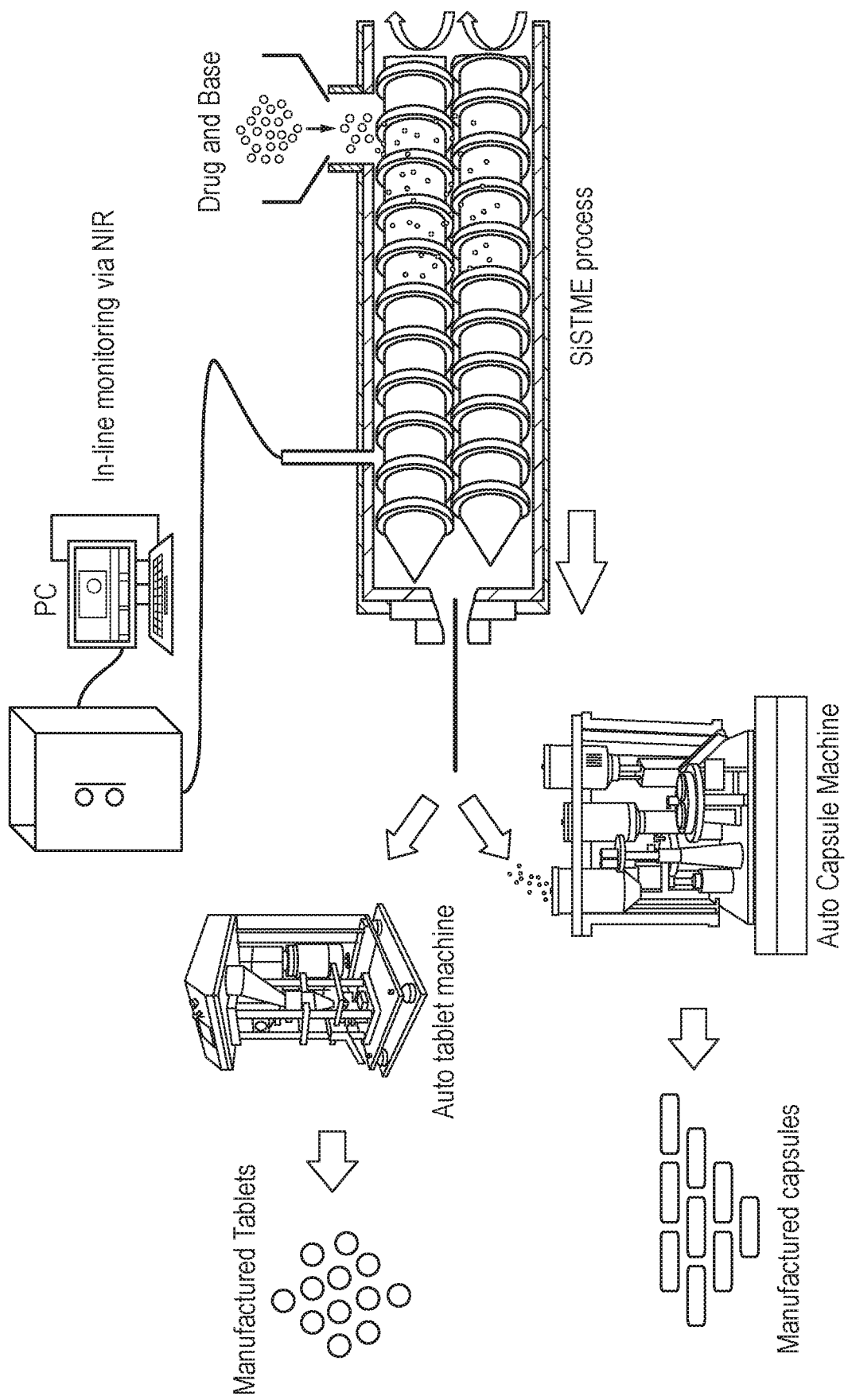
FIG. 2 is a scheme showing how the process of the invention can be useful in directly manufacturing tablets/capsules without any intermediate steps (e.g. blending with lubricants).
Figure 3:
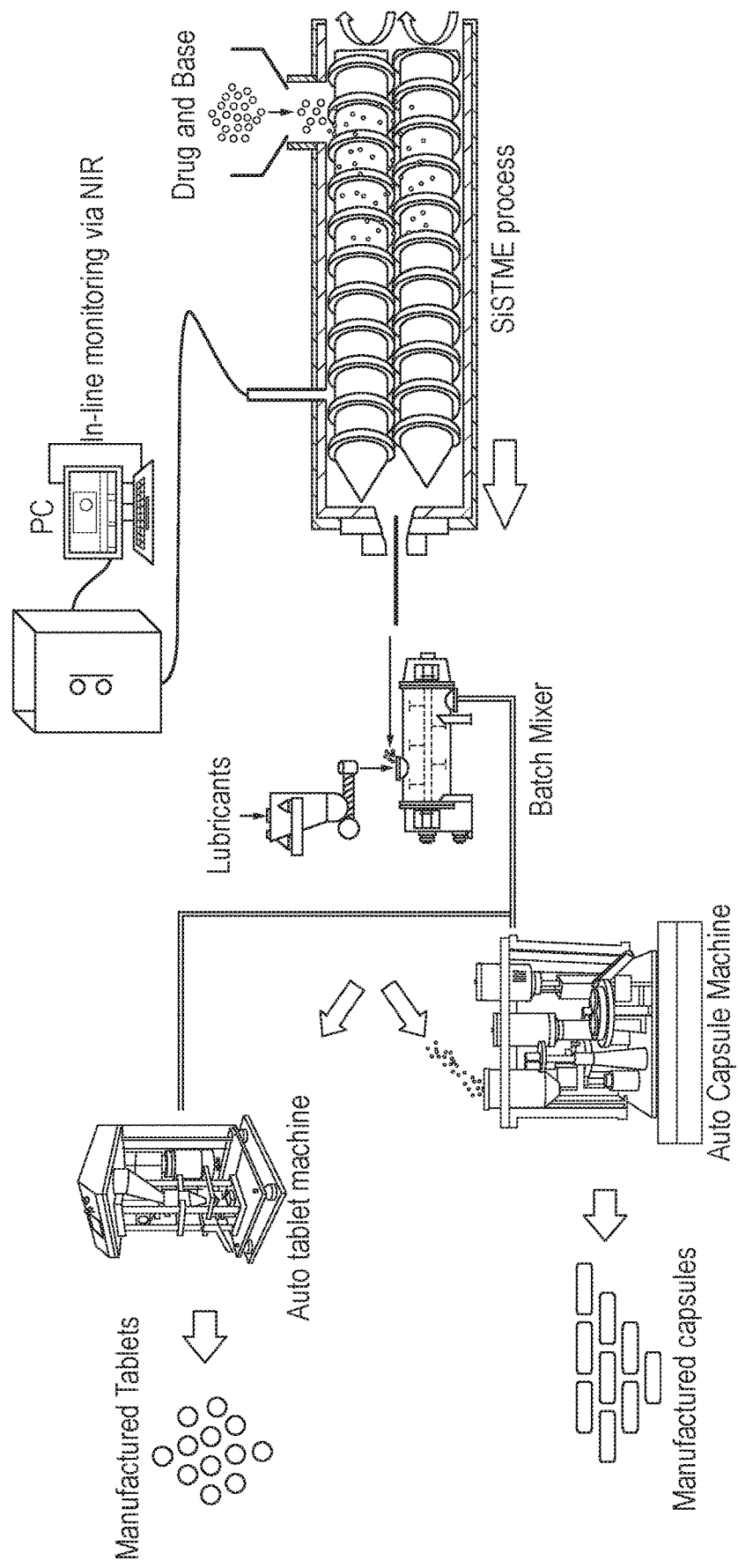
FIG. 3 is a scheme showing how the process of the invention can be useful in directly manufacturing orally disintegrating tablets/capsules with intermediate step (e.g. blending with lubricants).
Figure 4:
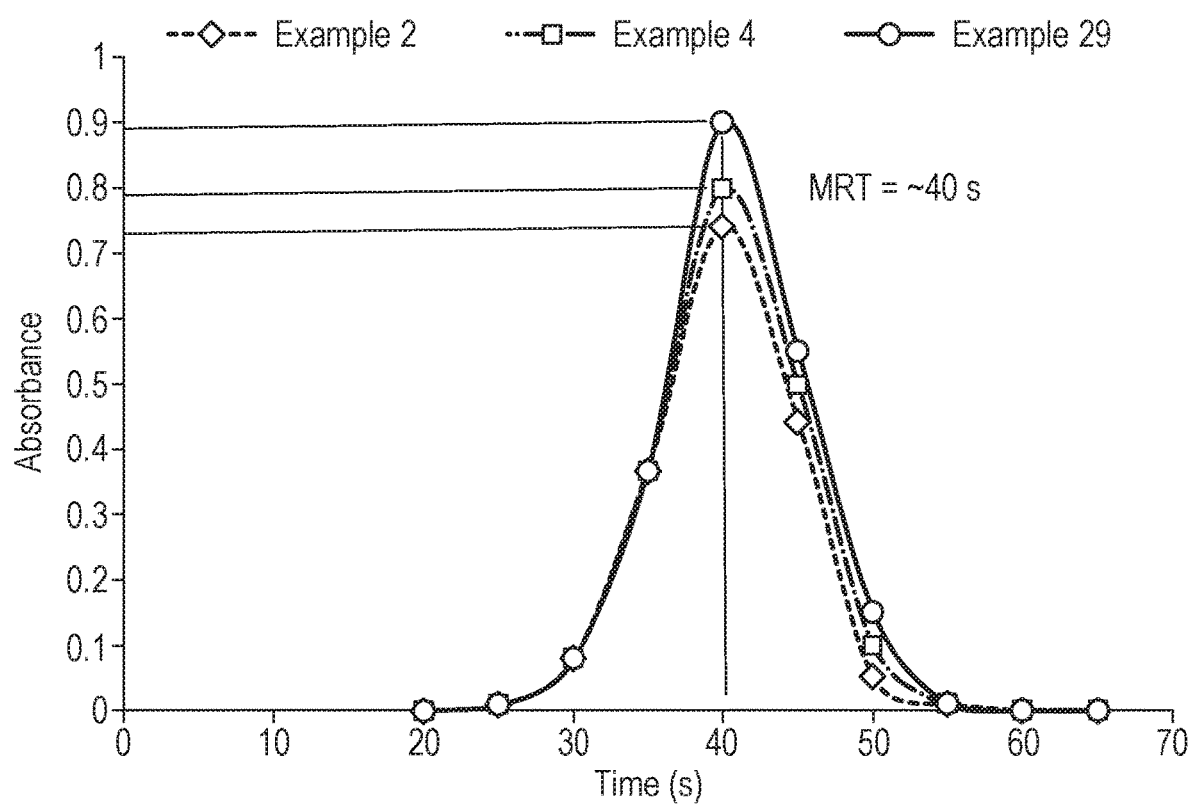
FIG. 4 shows Residence Time Distribution (RTD) and Mean Residence Time (MRT) for certain Examples. The examples shown in FIG. 4 are, in order of increasing peak absorbance, Examples 2, 4 and 29.
Figure 5A:
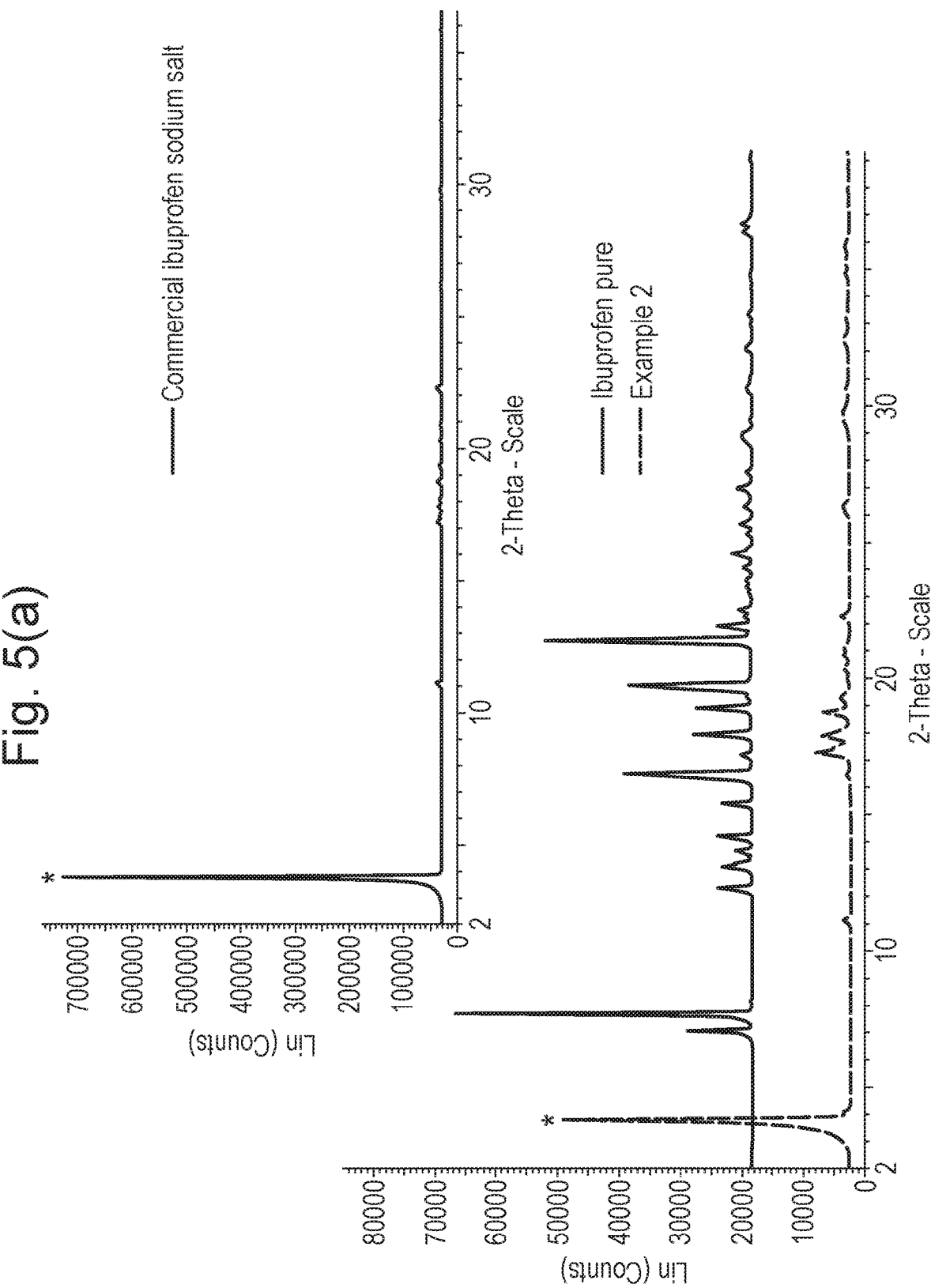
FIG. 5(a) shows XPRD diffractograms of, from top to bottom, a commercially-available ibuprofen salt, pure ibuprofen, and Example 2.
Figure 5C:
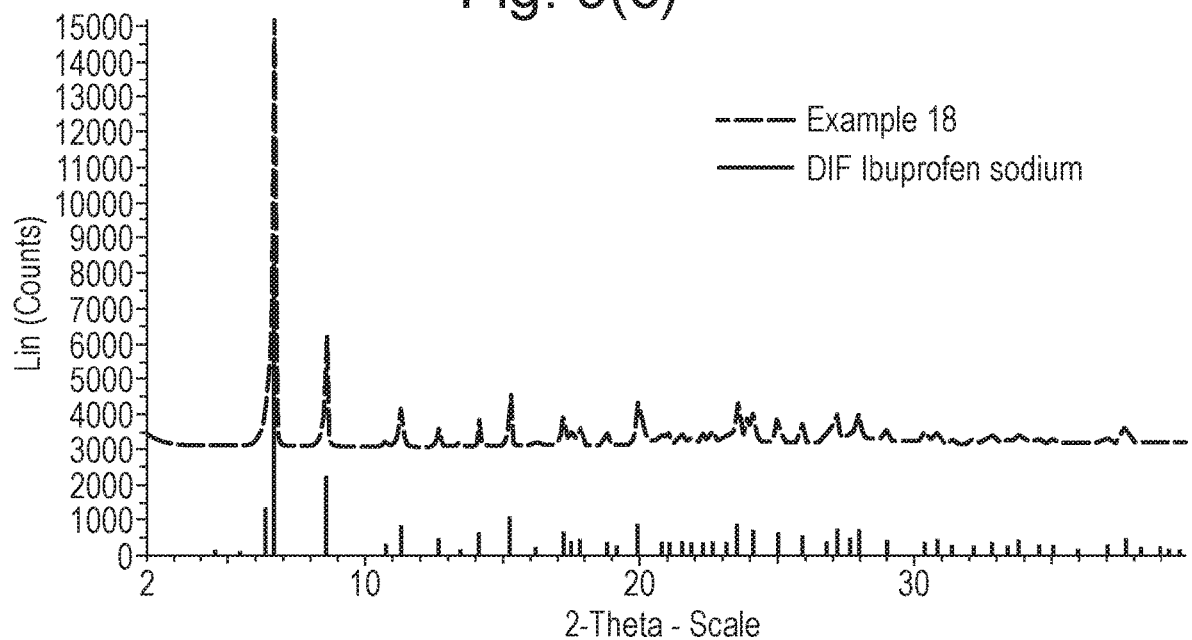
FIG. 5(c) shows XPRD diffractograms of, from top to bottom, Example 18 and commercially available diclofenac sodium.
Figure 5D:
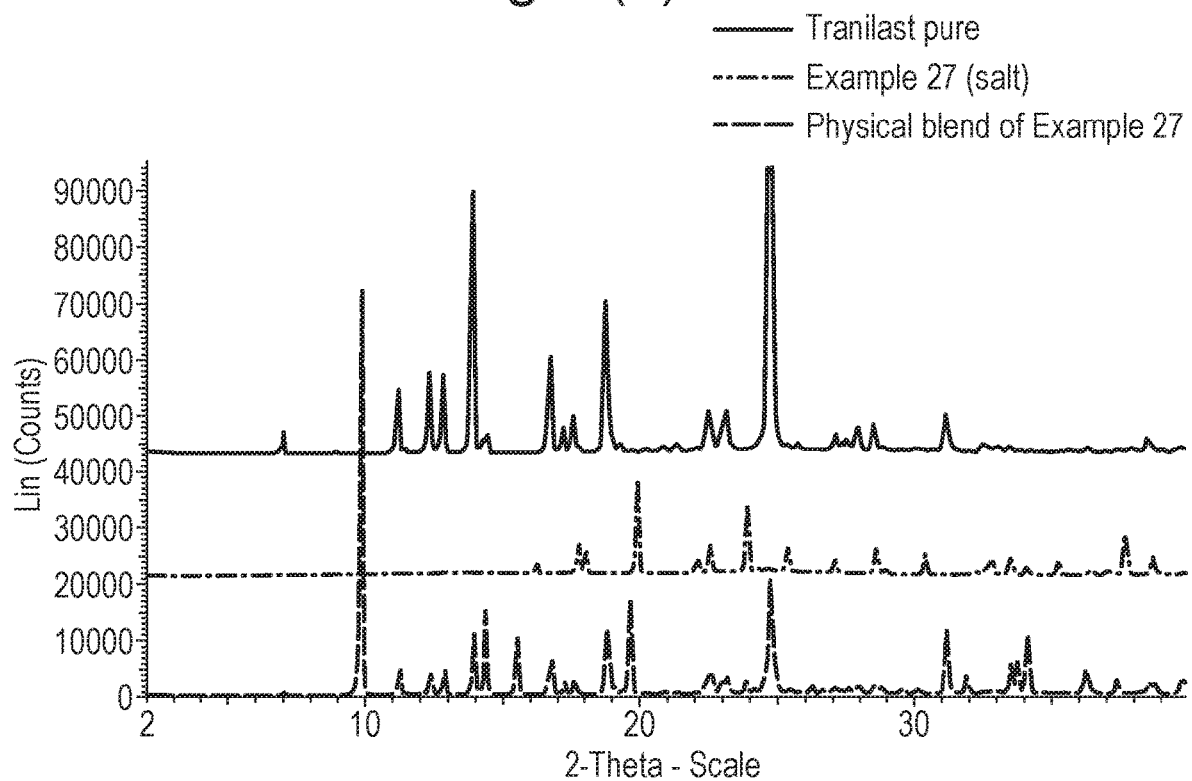
FIG. 5(d) shows XPRD diffractograms of, from top to bottom, pure tranilast, the composition of Example 27 and a physical blend of the components of Example 27
Figure 6A:
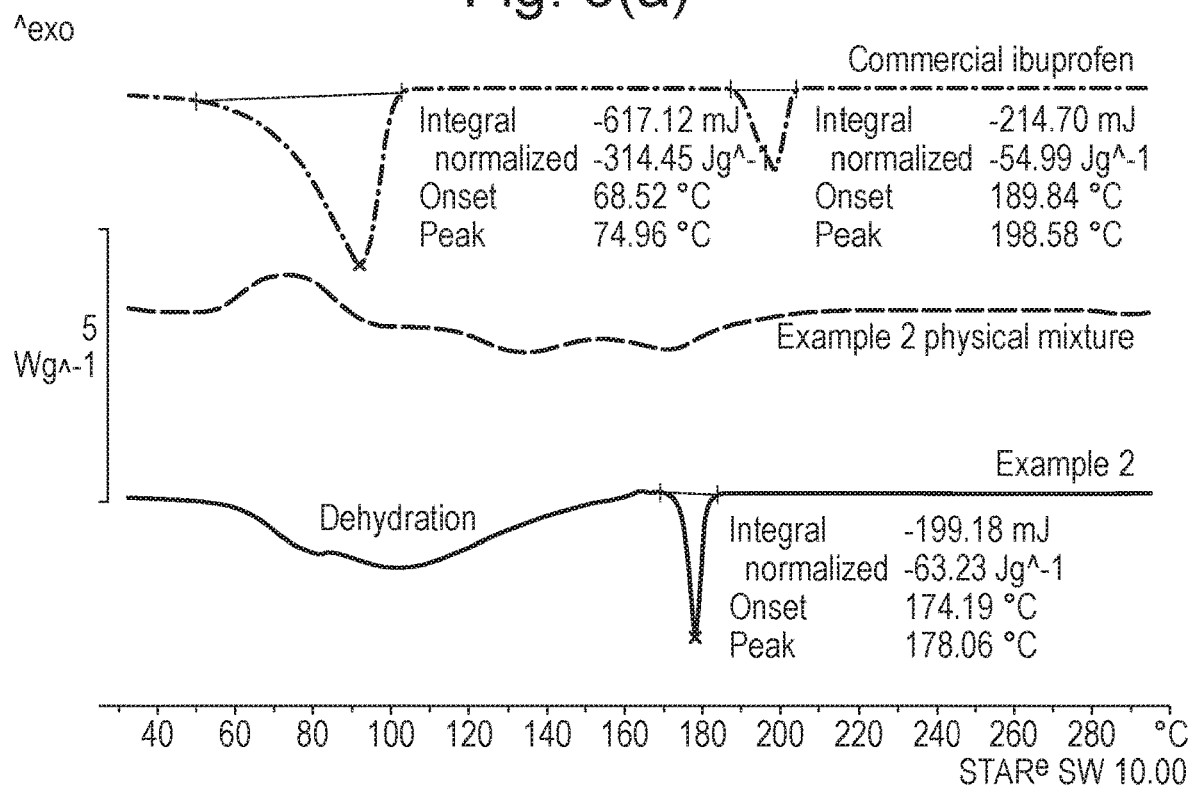
FIG. 6(a) shows DSC thermal transitions of commercially available ibuprofen, a physical mixture of the components of Example 2, and Example 2.
Figure 6B:
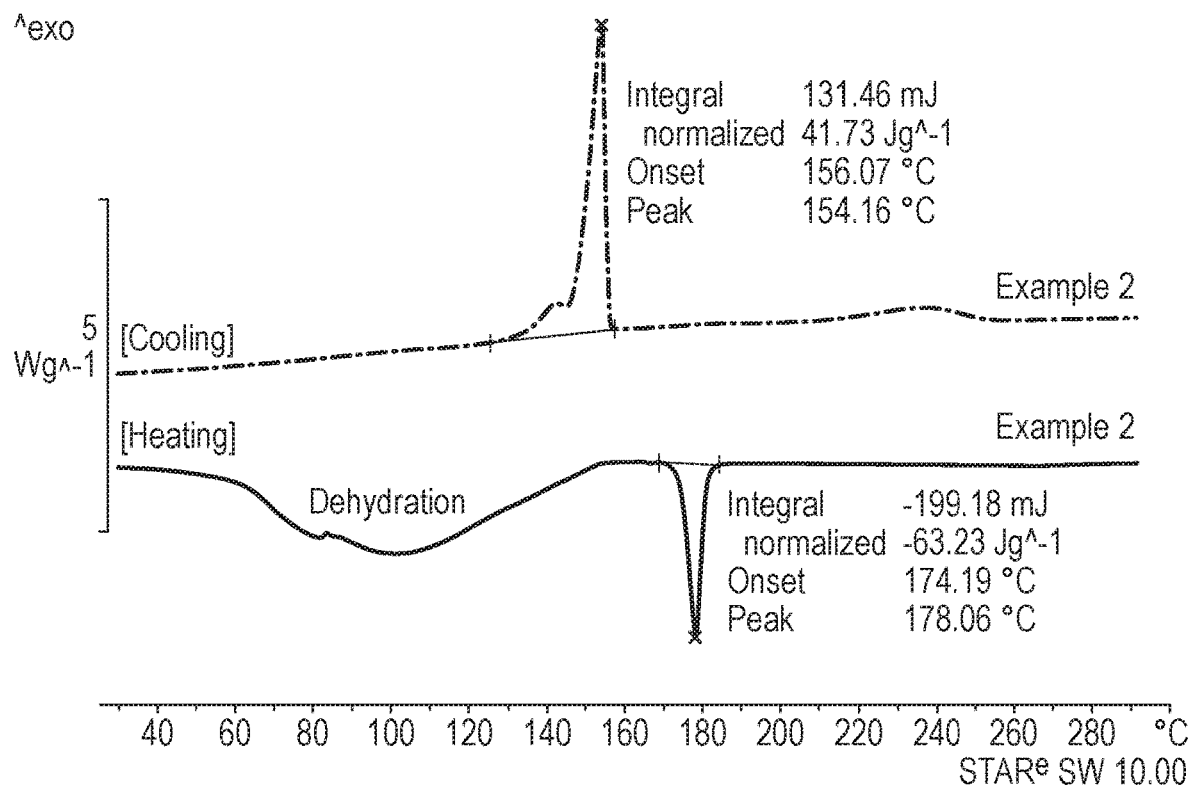
FIG. 6(b) shows thermal transitions of Example 2 for melting and recrystallization.
Figure 6C:
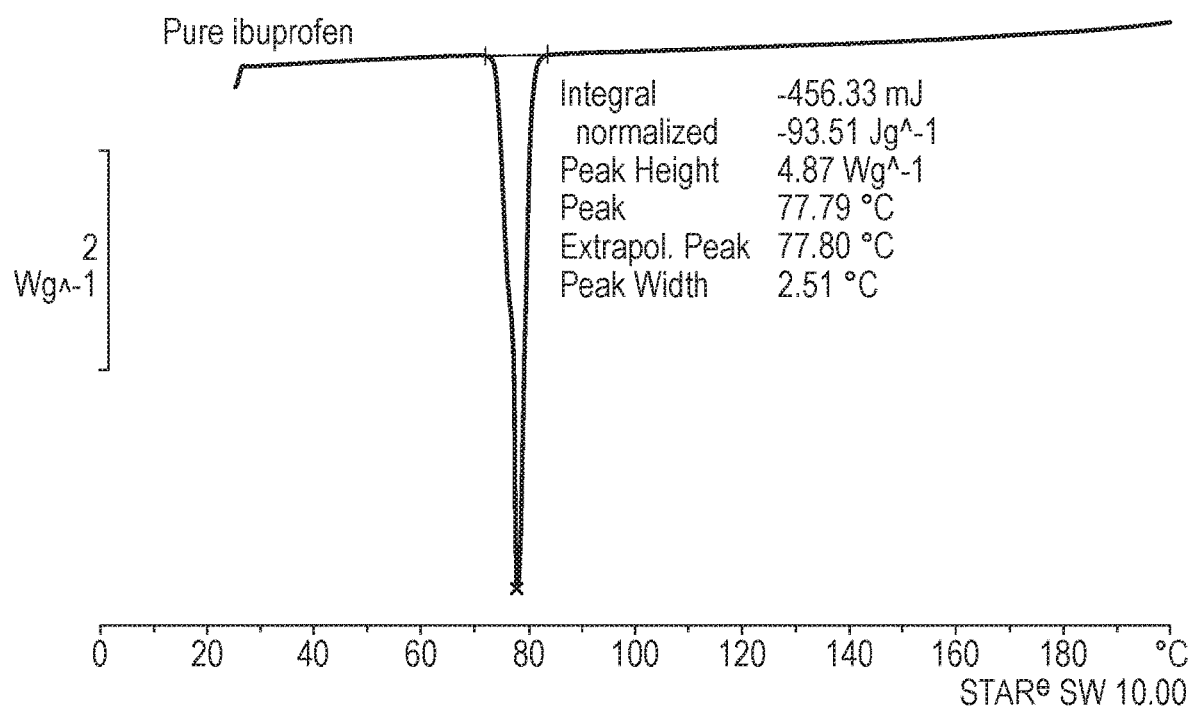
FIG. 6(c) shows thermal transitions of ibuprofen in bulk form.
Figure 6D:
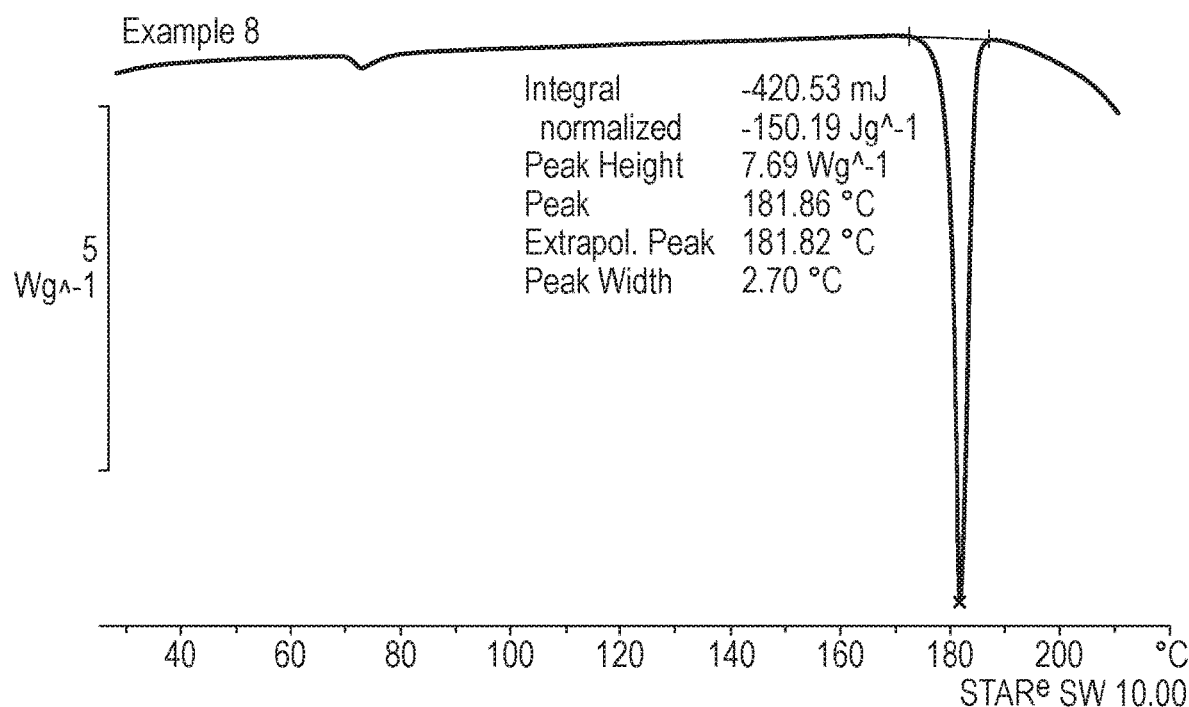
FIG. 6(d) shows thermal transitions of Example 8.
Figure 6E:
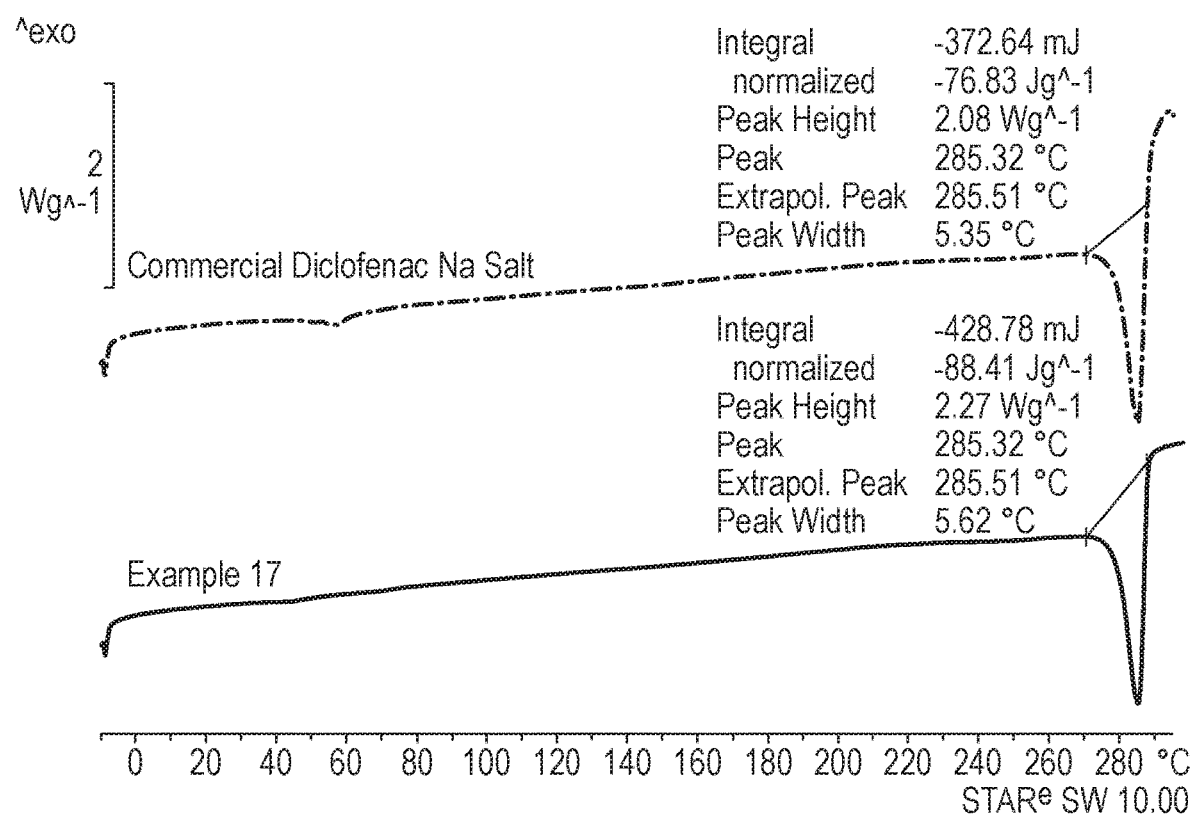
FIG. 6(e) shows thermal transitions of commercially available diclofenac sodium salt and Example 17.
Figure 7:
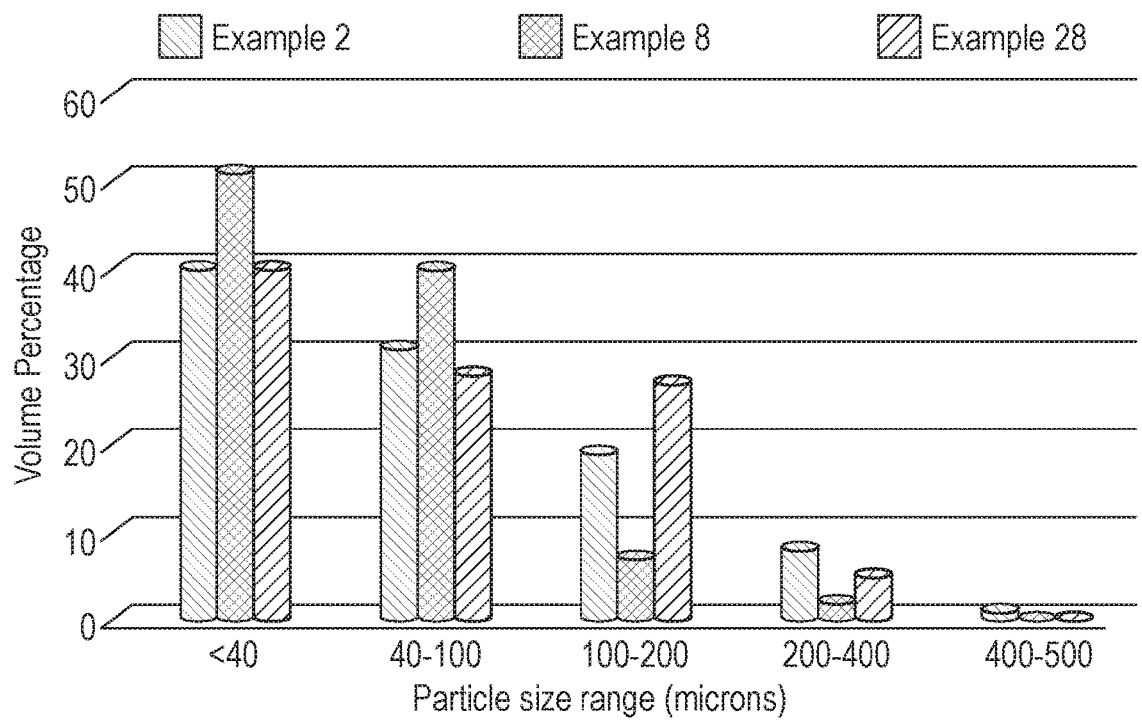
FIG. 7 shows particle size analysis of Examples 2, 8 and 28.
Figure 8:
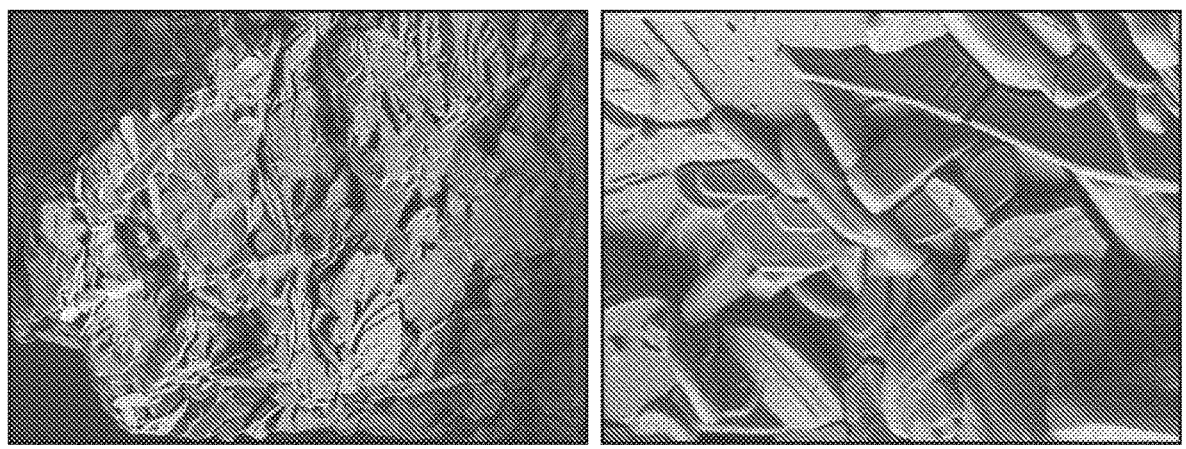
FIG. 8 shows SEM images of Example 2
Figure 9:
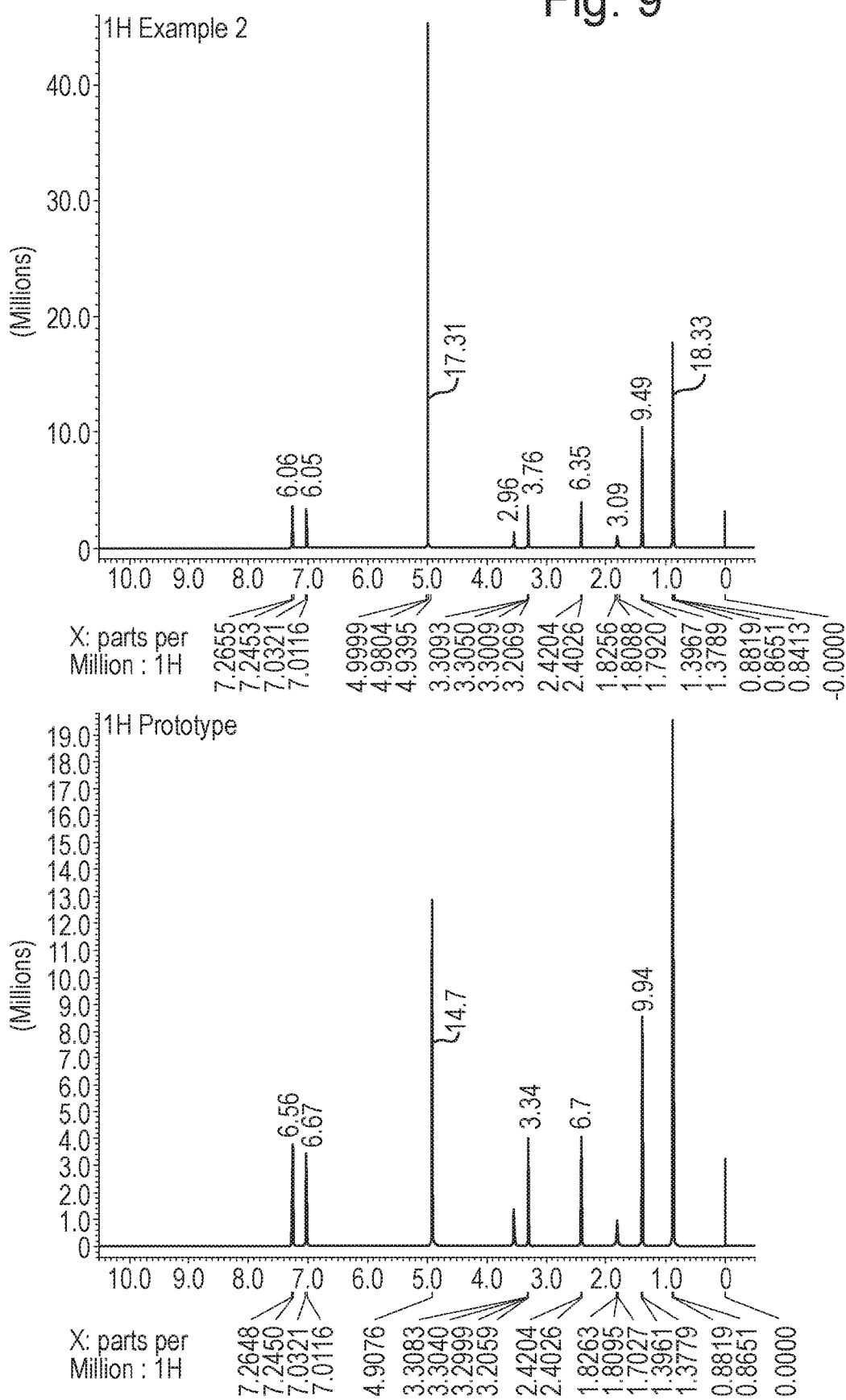
FIG. 9 shows NMR results for, from left to right, Example 2 and commercially available ibuprofen.
Figure 10:
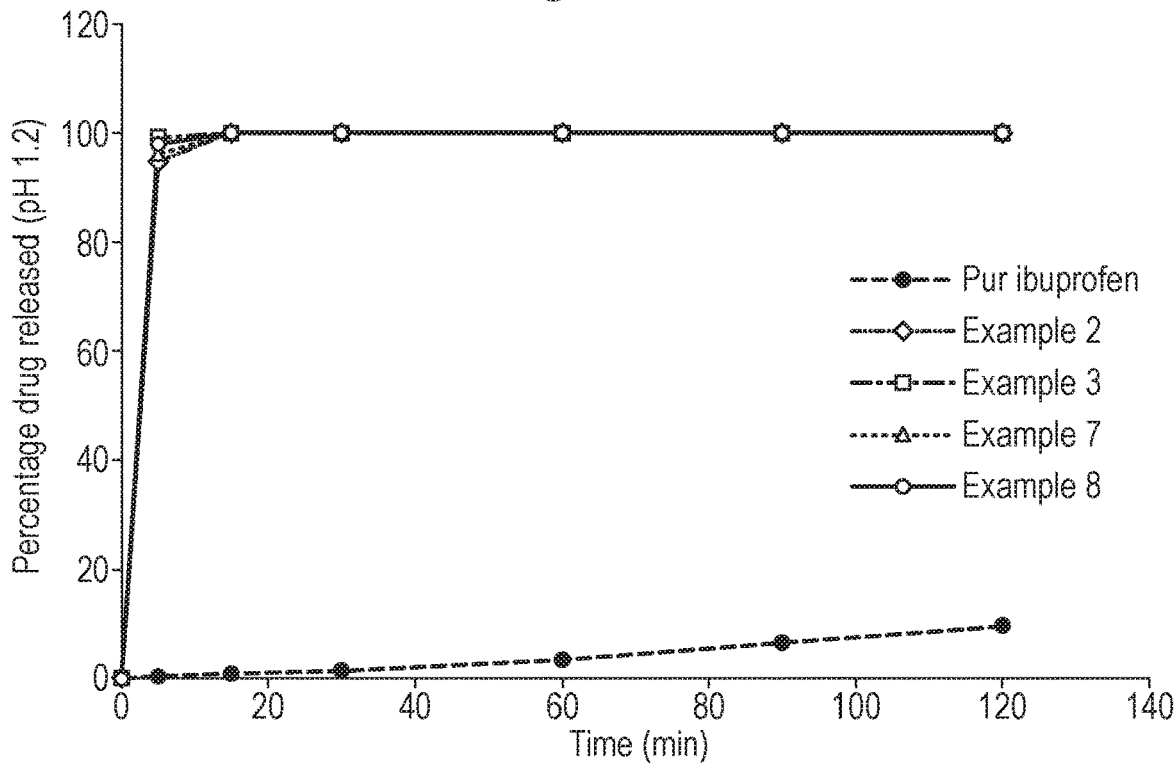
FIG. 10 shows results of in vitro dissolution studies (pH 1.2) for, from top to bottom at t=5s, Examples 3, 8, 7 and 2, and pure ibuprofen.
Figure 11:
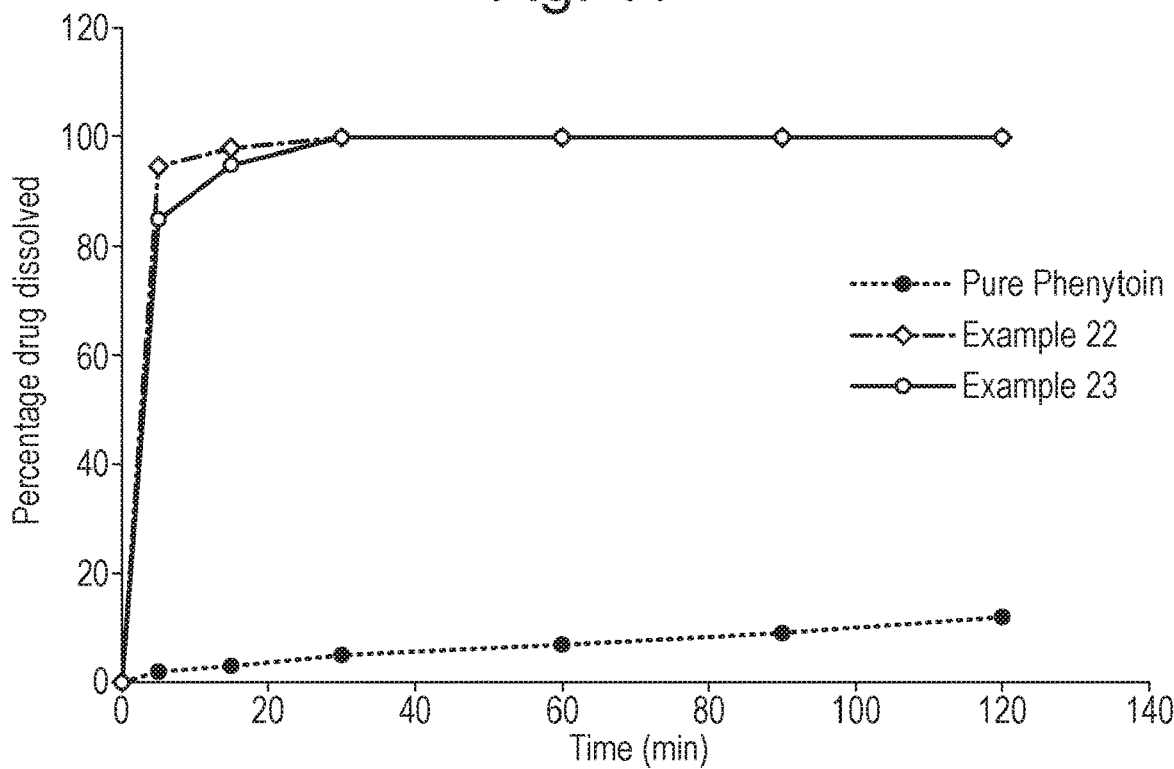
FIG. 11 shows results of in vitro dissolution studies (pH 1.2) for, from top to bottom at t=5s, Examples 22 and 23 and pure phenytoin.
Figure 12:
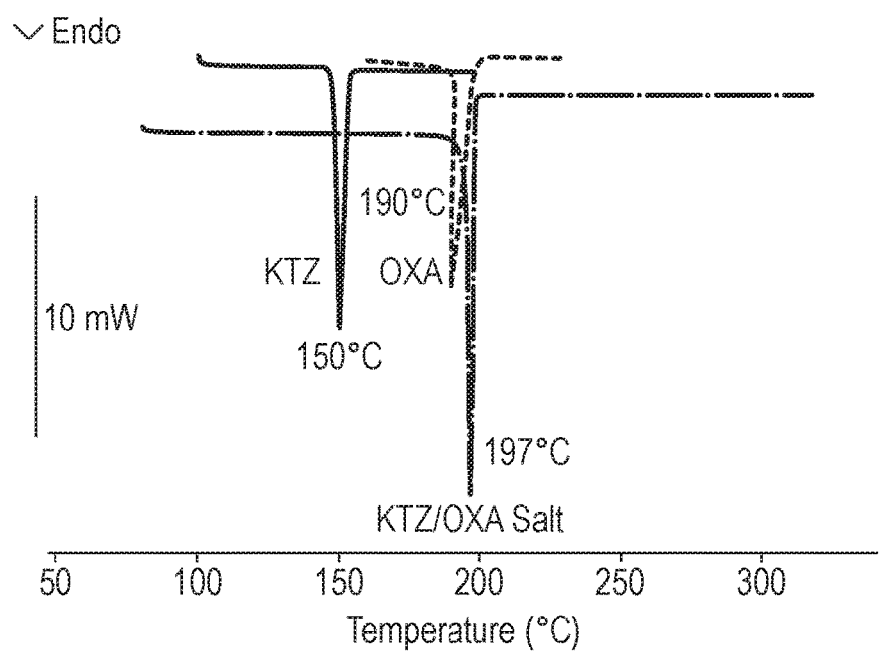
FIG. 12 shows thermal transitions of ketoconazole (KTZ), oxalic acid (OXA) and ketoconazole oxalate salt (KTZ/OXA) prepared according to the process of the present invention.
Figure 13:
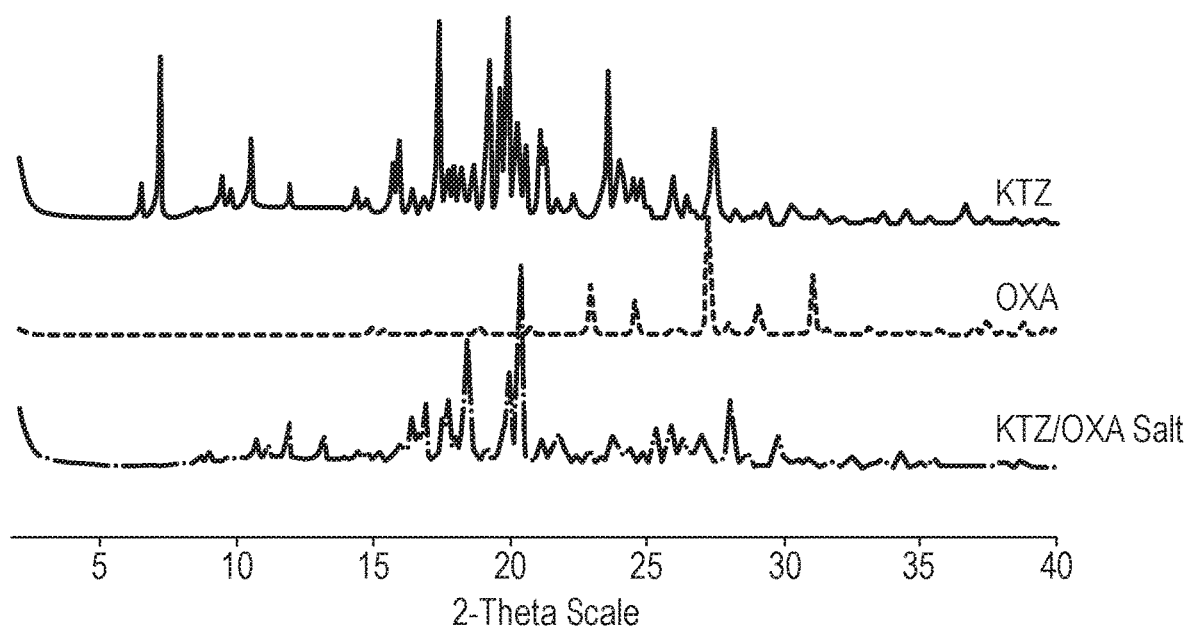
FIG. 13 shows XRD diffractograms of ketoconazole (KTZ), oxalic acid (OXA) and ketoconazole oxalate salt (KTZ/OXA) prepared according to the process of the present invention.

In this process the extrusion die is removed and the granules are obtained as a free flowing powder. All trials were conducted using a EuroLab 16 twin screw extruder (ThermoFisher, Germany) and all as extruded free flowing powders were suitable to incorporate into final tablet formulations (FIGS. 2 and 3).

Normal and Orally Disintegrating Tablet (ODT) Preparation

Batches were prepared using batch sizes of 100 g. All materials (see Tables 2-4) were passed through a mesh sieve with an aperture of 500 µm before use. Where included, the batches were blended with sodium stearyl fumarate (1%) in a Turbula TF2 mixer (Basel, Switzerland) for 10 minutes. Blends were directly compressed on a Flexitab trilayer tablet press (Oystar-Manesty, Germany) using 13 mm normal flat punches. Dwell time was set at 30 ms and the compaction force varied from 8-12 kN to obtain tablets of about 3 mm thickness (average weight 250-400 mg). All prepared ODTs were further evaluated to characterise the properties of the manufactured dosage forms (Table 5).

Formulations Processing Parameters

Temperature profiles for Ibuprofen—Temperature profiles (40° C.-80° C.-80° C.-100° C.-120° C.-120° C.-120° C.-120° C.-25° C. (±5° C., feeder→die); Screw speed 50-100 rpm; feed rate 1-7 kg/h.

Temperature for Diclofenac/Phenytoin/Ketoconazole—Temperature profiles (50° C.-170° C.-170° C.-180° C.-180° C.-180° C.-180° C.-180° C.-25° C. (±5° C., feeder→die); Screw speed 50-100 rpm; feed rate 0.5-7 kg/h.

Temperature for Lamotrigine—Temperature profiles (50° C.-170° C.-180° C.-200° C.-200° C.-200° C.-200° C.-200° C.-25° C. (±5° C., feeder→die); Screw speed 50-100 rpm; feed rate 0.5-5 kg/h.

TABLE 2

Extrusion compositions comprising pharmaceutical ingredient & salt forming substance

| Ingredients | Example 1 | Example 2 | Example 3 | Example 4 | Example 5 | Example 6 | Example 7 Molar Ratio | Example 8 | Example 9 | Example 10 | Example 11 | Example 12 | Example 13 | Example 14 |
|---|---|---|---|---|---|---|---|---|---|---|---|---|---|---|
| Ibuprofen | 1 | 1 | 1 | 2 | 1 | 1 | 1 | 1 | 1 | 2 | 1 | 1 | 1 | 1 |
| Diclofenac | | | | | | | | | | | | | | |
| Phenytoin | | | | | | | | | | | | | | |
| Tranilast | | | | | | | | | | | | | | |
| NaOH | 1 | 2 | 3 | 3 | | | | | | | | | | |
| KOH | | | | | 2 | 3 | | | | | | | | |
| Ca(OH)$_2$ | | | | | | | | | 1 | 3 | | | | |
| Na$_2$CO$_3$ | | | | | | | | | | | | | | |
| K$_2$CO$_3$ | | | | | | | 2 | 3 | | | | | | |
| Sodium Lysinate | | | | | | | | | | | 1 | 3 | | |
| Pottasium Lysinate | | | | | | | | | | | | | | |
| Tribasic sodium | | | | | | | | | | | | | 1 | |
| Potassium phospahte | | | | | | | | | | | | | | 2 |
| Tartaric Acid | | | | | | | | | | | | | | |

| Ingredients | Example 15 | Example 16 | Example 17 | Example 18 | Example 19 | Example 20 | Example 21 Molar Ratio | Example 22 | Example 23 | Example 24 | Example 25 | Example 26 | Example 27 | Example 28 |
|---|---|---|---|---|---|---|---|---|---|---|---|---|---|---|
| Diclofenac | 1 | 2 | 1 | 1 | | | | | | | | | | |
| Phenytoin | | | | | 1 | 1 | 2 | 1 | 1 | 1 | | | | |
| Tranilast | | | | | | | | | | | 1 | 2 | 1 | 1 |
| NaOH | | | 2 | 3 | | | | 2 | 3 | | 2 | 2 | 2 | 3 |
| KOH | | | | | | | | | | | | | | |
| Ca(OH)$_2$ | | | | | | | | | | | | | | |
| Na$_2$CO$_3$ | 2 | 3 | | | | | | 1 | | 2 | | | | |
| K$_2$CO3 | | | | | | | 1 | | | | | | | |
| Sodium Lysinate | | | | | | | | | | | | | | |
| Pottasium Lysinate | | | | | | | | | | | | | | |
| Tribasic sodium | | | | | 2 | 3 | 5 | | | | | | | |
| Potassium phospahte | | | | | | | | | | | | | | |
| Tartaric Acid | | | | | | | | | | | 1 | 1 | 2 | 3 |

| Ingredients | Example 29 | Example 30 | Example 31 Molar ratio | Example 32 | Example 33 | Example 34 | Example 35 | Example 36 | Example 37 | Example 38 | Example 39 | Example 40 | Example 41 | Example 42 |
|---|---|---|---|---|---|---|---|---|---|---|---|---|---|---|
| Ibuprofen | 1 | 1 | 1 | 1 | 1 | 1 | | | | | | | | |
| Diclofenac | | | | | | | | | | | | | | |
| Ketoconazole | | | | | | | 0.9 | 1 | 1 | 0.45 | 1 | 1 | | |
| Lamotrigine | | | | | | | | | | | | | 1 | 1 |
| Tranilast | | | | | | | | | | | | | | |
| NaOH | | | | | | | | | | | | | | |
| KOH | | | | | | | | | | | | | | |
| Ca(OH)$_2$ | | | | | | | | | | | | | | |
| Na$_2$CO$_3$ | | | | | | | | | | | | | | |
| K$_2$CO3 | | | | | | | | | | | | | | |
| Sodium Lysinate | | | | | | | | | | | | | | |
| L-Arginine | 0.8 | 0.9 | 1 | 1.1 | 1.2 | 2 | | | | | | | | |
| Oxalic acid | | | | | | | 1 | 1 | 1.1 | 0.55 | 1.5 | 2 | | |
| Saccharin | | | | | | | | | | | | | 1 | 2 |
| Pottasium Lysinate | | | | | | | | | | | | | | |
| Tribasic sodium | | | | | | | | | | | | | | |
| Potassium phospahte | | | | | | | | | | | | | | |
| Tartaric Acid | | | | | | | | | | | | | | |

TABLE 3

Conventional Tablet Compositions without any other excipients

| Ingredients | Example 2 (% w/w) | Example 3 (% w/w) | Example 7 (% w/w) | Example 8 (% w/w) | Example 15 (% w/w) | Example 18 (% w/w) | Example 21 (% w/w) | Example 22 (% w/w) | Example 23 (% w/w) | Example 25 (% w/w) | Example 26 (% w/w) | Example 28 (% w/w) | Example 29 (% w/w) | Example 32 (% w/w) |
|---|---|---|---|---|---|---|---|---|---|---|---|---|---|---|
| Salts | 98 | 100 | 98 | 98 | 99 | 98 | 99.5 | 99 | 98 | 98 | 95 | 99 | 99 | 99 |
| MgSt | 1 | — | 1 | 1 | 0.8 | 1.5 | 0.5 | 0.5 | 1 | 0.5 | 1 | 0.5 | 0.5 | 0.5 |
| SiO2 | 1 | — | 1 | 1 | 0.2 | 0.5 |  | 0.5 | 1 | 1.5 | 4 | 0.5 | 0.5 | 0.5 |

TABLE 4

ODTs compositions

| Ingredients | Example 2 (% w/w) | Example 3 (% w/w) | Example 7 (% w/w) | Example 8 (% w/w) | Example 15 (% w/w) | Example 18 (% w/w) | Example 21 (% w/w) | Example 22 (% w/w) | Example 23 (% w/w) | Example 25 (% w/w) | Example 26 (% w/w) | Example 28 (% w/w) | Example 29 (% w/w) | Example 32 (% w/w) |
|---|---|---|---|---|---|---|---|---|---|---|---|---|---|---|
| Salts | 71.4 | 71.4 | 71.4 | 71.4 | 71.4 | 83.33 | 66.67 | 66.67 | 83.33 | 83.33 | 79.11 | 79.11 | 83.33 | 79.11 |
| Pearlitol/sorbitol | 6.1 |  | 7 | 7.6 | 12.6 |  |  |  |  |  |  |  |  |  |
| Xl 10 Xl | 15 |  |  | 20 |  |  | 20 |  | 15.67 |  | 19.88 |  |  | 19.88 |
| Vivasol |  | 20 |  |  |  |  |  | 20 |  | 15.67 |  |  |  |  |
| Kollidon Cl- SF |  |  | 10 |  |  |  |  |  |  |  |  |  | 15.67 |  |
| Kollidon Cl- MF |  |  |  |  | 15 | 15.67 |  |  |  |  |  | 19.88 |  |  |
| PRUV |  | 1 | 1 | 1 | 1 | 1 | 1 | 1 | 1 | 1 | 1 | 1 | 1 | 1 |
| MgSt | 0.8 |  |  |  |  |  |  |  |  |  |  |  |  |  |
| SiO2 | 0.2 |  |  |  |  |  |  |  |  |  |  |  |  |  |

Evaluation of Tablets: Protocols

All prepared tablets were evaluated for the uniformity of thickness, hardness (Erweka TBH 28, Frankfurt, Germany), friability (Erweka friabilator, model A3R, Frankfurt, Germany), and disintegration time (Erweka, model ZT4, Heusenstamm, Germany) according to USP22 tests. The results are shown in Table 5.

In Vivo Drug Disintegration

In vivo disintegration and taste masking evaluation was performed by a panel of 6 healthy human volunteers from whom written consent was first obtained (approved by the Ethics Committee of the University of Greenwich). The study is also in accordance to the Code of Ethics of the World Medical Association (Declaration of Helsinki). The healthy volunteers of either sex (age 18-25) were selected, trained and the one tablet was held in the mouth after rinsing and the time required for complete disintegration of the tablet was recorded. The time when the tablet placed on the tongue disintegrated without leaving any lumps was taken as the end point. The disintegrated material was held in the mouth for another 60 seconds, and then spat out. The mouth was rinsed with water without swallowing the disintegrated material and, finally, the roughness levels were recorded on a numerical scale ranging from 1 to 5 where 1, 2, 3, 4 and 5 indicate no, slight, threshold, moderate, and high roughness, respectively. The results are shown in Table 5.

In Vitro Dissolution Tests

Results obtained from in vitro dissolution studies (pH 1.2) were obtained. All manufactured salts showed faster release compared to that of pure active ingredients. The dissolution rate of the poorly water soluble ibuprofen was increased 30 folds in Example 1 or 2 compared to that of pure ibuprofen.

TABLE 5

Properties of prepared ODTs from Table 4

| Formulations | Hardness (Kp) | Friability (%) | Disintegration Time (s) In vitro | Disintegration Time (s) In vivo |
|---|---|---|---|---|
| Example 2 | 9.6 ± 0.5 | 0.9 | 5 ± 0.2 | 9 ± 0.2 |
| Example 3 | 10.6 ± 0.5 | 0.8 | 6 ± 0.2 | 11 ± 0.2 |
| Example 7 | 11.6 ± 0.5 | 0.7 | 4 ± 0.2 | 9 ± 0.2 |
| Example 8 | 10.6 ± 0.5 | 0.9 | 3 ± 0.2 | 10 ± 0.2 |
| Example 15 | 8.6 ± 0.5 | 1.0 | 6 ± 0.2 | 12 ± 0.2 |
| Example 18 | 10.6 ± 0.5 | 0.9 | 5 ± 0.2 | 12 ± 0.2 |
| Example 21 | 8.6 ± 0.5 | 0.6 | 5 ± 0.2 | 9 ± 0.2 |
| Example 22 | 8.9 ± 0.5 | 0.8 | 6 ± 0.2 | 13 ± 0.2 |
| Example 23 | 9.6 ± 0.5 | 0.8 | 4 ± 0.2 | 8 ± 0.2 |
| Example 25 | 10.6 ± 0.5 | 0.7 | 7 ± 0.2 | 13 ± 0.2 |
| Example 26 | 9.6 ± 0.5 | 0.8 | 6 ± 0.2 | 13 ± 0.2 |
| Example 28 | 11.0 ± 0.5 | 0.6 | 5 ± 0.2 | 11 ± 0.2 |
| Example 29 | 10.10 ± 0.5 | 0.6 | 5 ± 0.2 | 12 ± 0.2 |
| Example 35 | 9.7 ± 0.5 | 0.8 | 9 ± 0.2 | 17 ± 0.2 |

The invention claimed is:

1. A process of preparing a salt of an active pharmaceutical ingredient, the process comprising providing a blend of an active pharmaceutical ingredient and a salt forming substance, mixing the blend in an extruder or a granulator with a heated barrel, optionally in the presence of added water, wherein at least a portion of the heated barrel is heated to a temperature of between 100° C. and 200° C., to react the active pharmaceutical ingredient with the salt forming substance to provide the salt of the active pharmaceutical ingredient in a free flowing powder form;

wherein when the active pharmaceutical ingredient is acidic, the salt forming substance is a base and the pKa difference between the acidic active pharmaceutical ingredient and the base is greater than 1; or when the active pharmaceutical ingredient is basic, the salt forming substance is an acid and the pKa difference between the basic active pharmaceutical ingredient and the acid is greater than 1;

wherein the process comprises directly compressing the salt of the active pharmaceutical ingredient in the free flowing powder form to form an orally disintegrating tablet without a further granulation or micronization step wherein the process is a continuous process;

and wherein a molar ratio of the salt forming substance to active pharmaceutical ingredient provided in the blend is 1:1 or higher.

2. The process of claim 1, wherein the mixing is carried out in a twin screw extruder or a single screw extruder.

3. The process of claim 1, wherein the process does not comprise adding additional water or solvent.

4. The process of claim 1, wherein the process does not comprise a drying step.

5. The process of claim 1, wherein the mixing is carried out in a twin screw extruder with a modified screw configuration to facilitate dispersive and distributive mixing via the generated shear force and stress inside the heated barrel.

6. The process of claim 1 wherein the process comprises manufacturing the orally disintegrating tablets with or without the addition of a hydrophilic polymer, super disintegrant, glidant, filler or lubricant.

7. The process of claim 1, wherein the free flowing powder of the salt of the active pharmaceutical ingredient is blended with a lubricant and then directly compressed to provide the orally disintegrating tablet.

8. The process of claim 1, wherein when the active pharmaceutical ingredient is acidic, the pKa difference between the acidic active pharmaceutical ingredient and the base is greater than 2.

9. The process of claim 1, wherein when the active pharmaceutical ingredient is acidic, the pKa difference between the acidic active pharmaceutical ingredient and the base is greater than 3.

10. The process of claim 1, wherein when the active pharmaceutical ingredient is basic, the salt forming substance is an acid and the pKa difference between the basic active pharmaceutical ingredient and the acid is greater than 2.

11. The process of claim 1, wherein when the active pharmaceutical ingredient is basic, the salt forming substance is an acid and the pKa difference between the basic active pharmaceutical ingredient and the acid is greater than 3.

* * * * *